(12) United States Patent
Hill et al.

(10) Patent No.: US 7,591,979 B2
(45) Date of Patent: Sep. 22, 2009

(54) ENHANCED MONITOR SYSTEM FOR WATER PROTECTION

(75) Inventors: David E. Hill, Knoxville, TN (US); Miguel Rodriquez, Jr., Oak Ridge, TN (US); Elias Greenbaum, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 829 days.

(21) Appl. No.: 10/689,316

(22) Filed: Oct. 20, 2003

(65) Prior Publication Data

US 2005/0084419 A1    Apr. 21, 2005

(51) Int. Cl.
*G01N 21/00*    (2006.01)
*G01N 21/64*    (2006.01)

(52) U.S. Cl. .............. 422/82.08; 422/62; 422/68.1; 436/52

(58) Field of Classification Search .......... 422/62, 422/68.1, 82.08; 436/52
See application file for complete search history.

(56) References Cited

U.S. PATENT DOCUMENTS

| | | | |
|---|---|---|---|
| 3,170,299 A | 2/1965 | Clarke | |
| 4,089,209 A | 5/1978 | Grana et al. | |
| 4,300,855 A | 11/1981 | Watson | |
| 4,347,133 A * | 8/1982 | Brigante | 210/138 |
| 4,448,068 A | 5/1984 | Sutherland et al. | |
| 4,500,641 A | 2/1985 | van den Engh et al. | |
| 4,549,427 A | 10/1985 | Kolesar, Jr. | |
| H454 H | 4/1988 | Sickenberger et al. | |
| 4,752,226 A | 6/1988 | Akers et al. | |
| 4,768,390 A | 9/1988 | Baker et al. | |
| 4,906,440 A | 3/1990 | Kolesar, Jr. | |
| 4,942,303 A * | 7/1990 | Kolber et al. | 250/458.1 |
| 5,014,225 A | 5/1991 | Vidaver et al. | |
| H1344 H | 8/1994 | Baldauf et al. | |
| 5,532,679 A | 7/1996 | Baxter, Jr. | |
| 5,645,799 A * | 7/1997 | Shah et al. | 422/62 |

(Continued)

FOREIGN PATENT DOCUMENTS

CA    2265304    3/1999

(Continued)

OTHER PUBLICATIONS

G.H. Krause, et al "Chlorophyll Fluorescence & Photosynthesis: The Basics," Annu. Rev. Plant Physiol. Plant Mol. Biol (1991) V. 42, p. 313-49.

(Continued)

*Primary Examiner*—Jill Warden
*Assistant Examiner*—Paul S Hyun
(74) *Attorney, Agent, or Firm*—Scully, Scott, Murphy & Presser (57) ABSTRACT

An automatic, self-contained device for detecting toxic agents in a water supply includes an analyzer for detecting at least one toxic agent in a water sample, introducing means for introducing a water sample into the analyzer and discharging the water sample from the analyzer, holding means for holding a water sample for a pre-selected period of time before the water sample is introduced into the analyzer, and an electronics package that analyzes raw data from the analyzer and emits a signal indicating the presence of at least one toxic agent in the water sample.

15 Claims, 6 Drawing Sheets

U.S. PATENT DOCUMENTS

| | | | |
|---|---|---|---|
| 5,654,692 | A | 8/1997 | Baxter, Jr. et al. |
| 5,817,954 | A * | 10/1998 | Kahng et al. ............. 73/863.84 |
| 5,866,430 | A | 2/1999 | Grow |
| 5,922,183 | A | 7/1999 | Rauh |
| 5,965,882 | A | 10/1999 | Megerle et al. |
| 6,029,076 | A * | 2/2000 | Fiddian-Greene et al. ... 600/353 |
| 6,083,740 | A | 7/2000 | Kodo et al. |
| 6,119,630 | A | 9/2000 | Lobsiger et al. |
| 6,119,976 | A | 9/2000 | Rogers |
| 6,121,053 | A | 9/2000 | Kolber et al. |
| 6,316,268 | B1 | 11/2001 | Yang et al. |
| 6,402,031 | B1 | 6/2002 | Hall |
| 6,569,384 | B2 | 5/2003 | Greenbaum et al. |
| 2002/0102629 | A1* | 8/2002 | Greenbaum et al. ........... 435/34 |
| 2005/0065755 | A1* | 3/2005 | McCarter et al. ............ 702/188 |

FOREIGN PATENT DOCUMENTS

| | | |
|---|---|---|
| DE | 248433 A1 | 8/1987 |
| DE | 41 40 414 A1 | 6/1993 |
| DE | 19857792 A1 | 7/2000 |
| EP | 0811842 A1 | 12/1997 |
| WO | WO 99/32876 | 7/1999 |

OTHER PUBLICATIONS

G.H. Krause, et al "Photoinduced Quenching of Chlorophyll Fluorescence in Intact Chloroplasts & Algae," Biochimica et Biophysica Acta, V. 679, p. 116-124 (1982).

U. Schreiber et al. "Chlorophyll Fluorescence as a Nonintrusive Indicator for Rapid Assessment of In Vivo Photosynthesis," Ecological Studies, 100, p. 49-70 (1994).

Bernard Genty et al "The Relationship Between the Quantum Yield of Photosynthetic Electron Transport & Quenching of Chlorophyll Fluorescence," Biochimica et Biophysics Acta, 990, p. 87-92 (1989).

O. Van Kooten et al "The Use of Chlorophyll Fluorescence Nomenclature in Plant Stress Physiology," Photosynthesis Research, 15, p. 147-150 (1990).

G.E. Edwards et al "Can CO2 Assimilation in Maize Leaves be Predicted Accurately from Chlorophyll Fluorescence Analysis," Photosynthesis Res., 37, p. 89-102 (1993).

G.G.R. Seaton et al Chlorophyll Fluorescence as a Measure of Photosynthetic Carbon Assimilation, Proc.R.Soc.London Ser. B, 242, p. 17-108 (1995).

Martine Naessens et al "Fiber Optic Biosensor Using Chlorella Vulgaris for Determination of Toxic Compounds," Ecotoxicology and Env. Safety, 46, p. 181-185 (2000).

Heinz Walz, "Internet Web Site http://www.walz.com eg, http://www.walz.com/xepam.htm & http://www.walz.com/pamzta.htm".

G. Dubelaar et al "Design & First Results of CytoBuoy: A Wire-less Flow Cytometer for In Situ Analysis of Marine & Fresh Waters," Cytometer 37, p. 247-254 (1999).

R.K. Gelda et al "Estimating Oxygen Exchange Across the Air-Water Interface of a Hypereutrophic Lake," Hydrobiologia, 487, p. 243-254 (2002).

M. Rodriguez,Jr. et al "Biosensors for Rapid Monitoring of Pri-mary-Source Drinking Water Using Naturally Occurring Photo-synthesis," Biosensors & Bioelectronics 17, p. 843-849 (2002).

A. Pinto et al "Chlorophyll—A Determination via Continuous Measurement of Plankton Fluorescence:Methodology Development" Wat. Res. vol. 35, No. 16, p. 3977-3981 (2001).

C.A. Sanders et al "Stand-off Tissue-Based Biosensors for the Detection of Chemical Warfare Agents using Photosynthetic Fluorescence Induction", Biosensors & Bioelectronics 16 p. 439-446 (2001).

K. Wild-Allen et al "Observations of Diffuse Upwelling Irradiance & chlorophyll in Case I Waters Near the Canary Islands (Spain)" Optics & Laser Technology, V29, No. 1 p. 3-8 (1997).

T. Moore et al "Real-Time River Level Monitoring Using GPS Heighting," GPS Solutions, V. 4, No. 2, p. 63-67 (2000).

D. Lapota et al Development of an Autonomous Bioluminescence Buoy (BioBuoy) for Long-Term Ocean Measurements, SPAWAR Systems Center.

U.A. Korde, "A Note on the Hydrodynamics of a Tail Tube Buoy," Ocean Engineering 27, p. 1473-1484 (2000).

M. Kishino et al. "Verification Plan of Ocean Color & Temperature Scanner Atmospheric Correction ç Phytoplankton Pigment by Moored Optical Buoy System" Jl. of Geo. Res., V102,D14, p. 17, 197-17, 207 (1997).

Drinking Water Standards and Health Advisories, Office of Water U. S. Enrivonmental Protection Agency, Washington D.C. (2000).

J.W. Klett et al, "Flexible Towpreg for the Fabrication of High Thermal Conductivity Carbon/Carbon Composites," Carbon, V. 33, No. 10, p. 1485 1503 (1995).

Guidelines for Chemical Warfare Agents in Military Field Drinking Water, National Academy Press, Washington, D.C. (1995).

F. Jacques and Y. Boudey, "A Biosensor for Water Quality Monitoring," IEEE Instrumentation & Measurement Tech. Conf. Brussels, Belgium, 1996, pp. 1354-1358.

* cited by examiner

ENHANCED MONITOR SYSTEM FOR WATER PROTECTION

The United States Government has rights in this invention pursuant to contract no. DE-AC05-00OR22725 between the United States Department of Energy and UT-Battelle, LLC.

CROSS-REFERENCE TO RELATED APPLICATIONS

Specifically referenced is commonly assigned U.S. Pat. No. 6,569,384 issued on May 27, 2003 to Greenbaum, et al. entitled "Tissue-Based Water Quality Biosensors for Detecting Chemical Warfare Agents", the entire disclosure of which is incorporated herein by reference.

Also specifically referenced is commonly assigned U.S. patent application Ser. No. 10/689,261, now U.S. Pat. No. 7,258,836 B2, filed on even date herewith, entitled "Freeze resistant Buoy System", the entire disclosure of which is incorporated herein by reference.

FIELD OF THE INVENTION

The present invention relates to automatic, continuous water quality monitoring systems, and more particularly to water quality monitoring systems that employ means for holding a water sample prior to analysis to allow dark adaptation and/or settling of sediment to optimize chlorophyll fluorescence analysis of the sample.

BACKGROUND OF THE INVENTION

Recent terrorist attacks in the United States have increased the awareness of the need for ways to protect drinking water supplies. Source waters for civilian populations and military facilities are vulnerable to such attacks. There is therefore a need for improved water quality sensor systems that accurately detect toxic materials in real-time in a water source and transmit an indicative signal. Currently available systems for continuous, automatic monitoring of water quality by sensing changes in photosynthetic activity have no provision for availing dark adaptation of photosynthetic organisms before measurements are taken.

OBJECTS OF THE INVENTION

Accordingly, objectives of the present invention include provision of water quality monitoring systems that enable remote, rapid detection of toxic agents in water under real-world conditions, water quality monitoring systems that prevent freezing and/or overheating of the systems, water quality monitoring systems that delay analysis of water samples to allow dark adaptation and/or settling of sediment, and means for protecting water supplies, especially primary-source drinking water. Further and other objects of the present invention will become apparent from the description contained herein.

SUMMARY OF THE INVENTION

In accordance with one aspect of the present invention, the foregoing and other objects are achieved by an automatic, self-contained device for detecting toxic agents in a water supply that includes an analyzer for detecting at least one toxic agent in a water sample, introducing means for introducing a water sample into the analyzer and discharging the water sample from the analyzer, holding means for holding a water sample for a pre-selected period of time before the water sample is introduced into the analyzer, and an electronics package that analyzes raw data from the analyzer and emits a signal indicating the presence of at least one toxic agent in the water sample.

In accordance with another aspect of the present invention, a water quality monitor for detecting the presence of at least one toxic agent comprising: a fluorescence cell for analyzing photosynthetic activity of naturally occurring, indigenous photosynthetic organisms in water; means for introducing water into the cell and discharging water from the cell; a fluorometer for measuring photosynthetic activity of naturally occurring, indigenous photosynthetic organisms drawn into the cell; an electronics package that analyzes raw data from the fluorometer and emits a signal indicating the presence of at least one toxic agent in the water; and means for automatically delaying the analysis of a water sample for a sufficient time to allow dark adaptation of the organisms.

For a better understanding of the present invention, together with other and further objects, advantages and capabilities thereof, reference is made to the following disclosure and appended claims in connection with the above-described drawings.

DETAILED DESCRIPTION OF THE INVENTION

The present invention is a device (system) for automatically detecting toxic agents in source waters using chlorophyll fluorescence monitoring.

Figure 1:
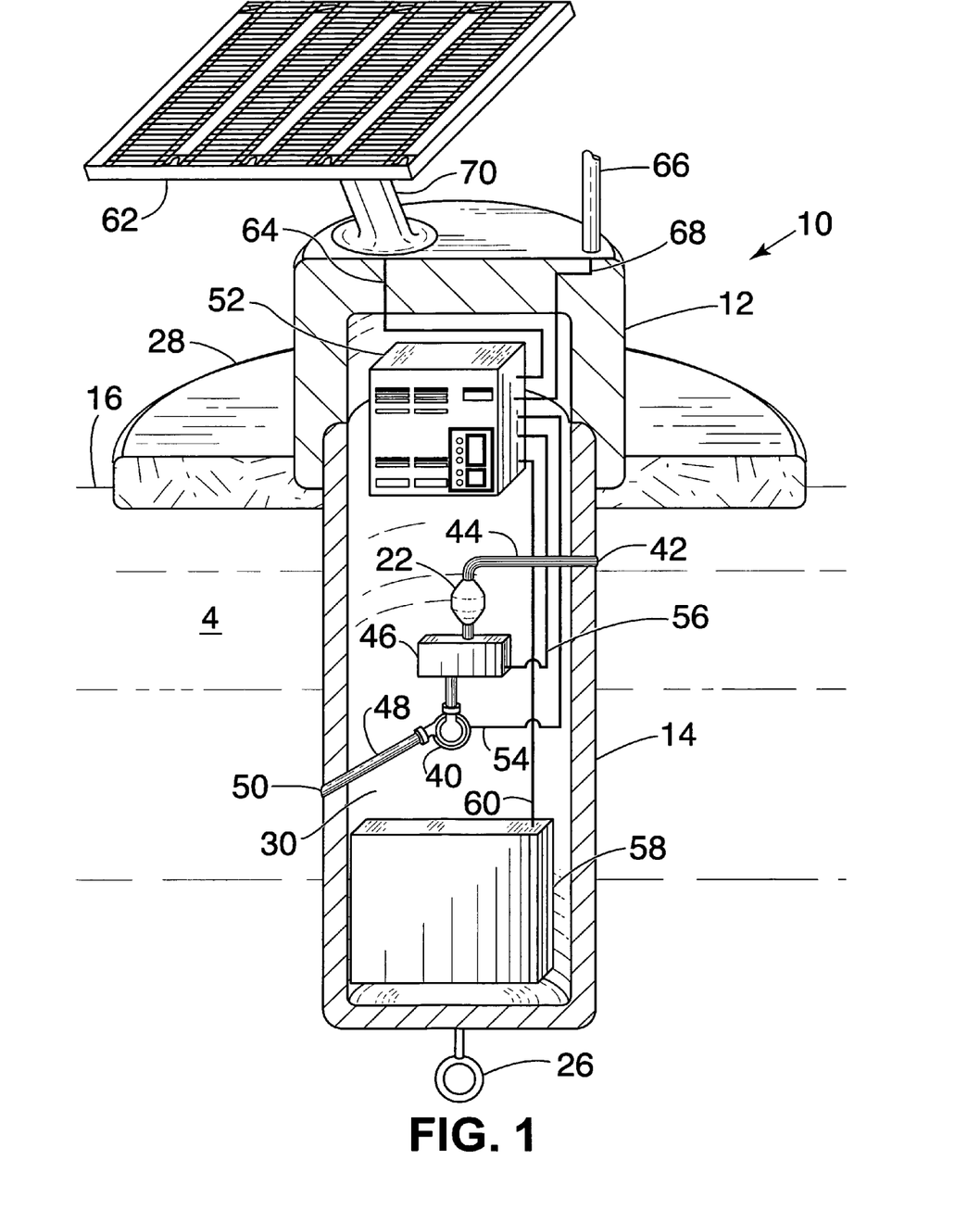
FIG. 1 is a cutaway view of an embodiment of the present invention that is suitable for use in a water supply containing relatively low levels of sediment.
Figure 2:
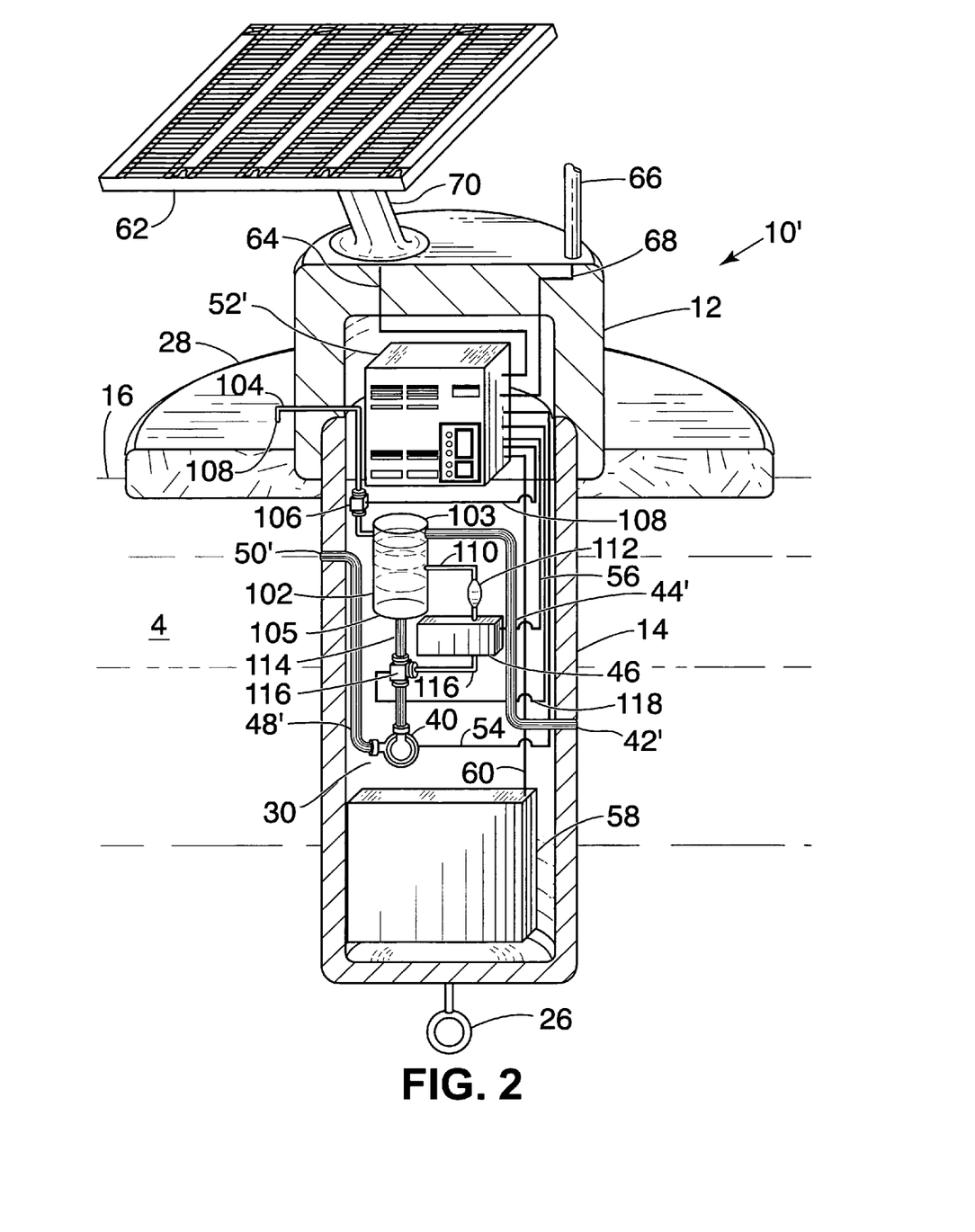
FIG. 2 is a cutaway view of an embodiment of the present invention that is suitable for use in a water supply containing relatively high levels of sediment.

Referring to FIGS. 1 and 2, essentially equivalent elements are identified with the same numerals. Elements that are similar, but may have some differences, are identified with the same numerals, but primed in FIG. 2. A tail-tube buoy 10, 10' respectively, houses the water quality monitoring system in the interior 30 thereof. The buoy 10, 10' comprises an upper section 12, which is disposed predominately above the waterline 16, and a lower section 14, which is disposed predominately below the waterline 16. An anchoring ring 26 is usually attached to the bottom of the buoy 10, 10'. A buoyant stabilizing wing or collar 28 is usually attached at the waterline 16.

FIG. 1 shows a simpler embodiment of the invention that is particularly suitable for bodies of water 4 that are relatively clear, or low in sediment. A pump 40 causes water to flow into the water quality monitoring system through an inlet 42, and influent tube 44, into a into a fluorometer 46, through an effluent tube, 48, and outlet 50. Location of the pump, inlet 42, outlet 50, and routing of the inlet and outlet tubes 44, 48 are not critical to the invention.

The fluorometer 46 is essentially as described in U.S. Pat. No. 6,569,384, referenced hereinabove. The inlet 42 may comprise a filter, screen, baffle, or other device to prevent solid materials from entering the influent tube 44. The pump 40 may be located anywhere along the inlet tube 44 or outlet tube 48. The pump 40 and fluorometer 46 are controlled by an electronics package 52 housed in the interior 30 and have respective electrical connections 54, 56 thereto.

A power supply 58, such as a deep-cycle battery, is also housed in the interior 30, and has electrical connection 60. A solar panel 62 or other device for harnessing natural energy is optionally mounted on the buoy 10, optionally with a support bracket 70 or the like, and has an electrical connection 64 to the electronics package 52, as shown, or directly to the power supply 58. The solar panel 62 preferably charges the battery 58. The electronics package 52 preferably monitors the power level, controls recharging cycles, and detects low battery and failure conditions. An antenna 66 is mounted on the buoy 10 and has an electrical connection 68 to the electronics package 52. The power supply 58 can also comprise a hydrogen fuel cell, wave motion or other electrical power technology that would improve efficiency of the device.

Operational cycle of the system begins with activation of the pump 40 to draw a fresh water sample into the fluorometer 46 and flush out any sediment that may have collected therein. The pump 40 will be deactivated, and there will be a pause for a period of dark adaptation. A period of dark adaptation is defined as the time required for the photosynthetic organisms to recover (partially or fully) from light-induced suppression of physiological activity. A pause of about 2 to about 6 minutes is suitable for most applications. A preferable pause is about 3 to about 5 minutes, and a more preferable pause is about 4 minutes.

The addition of an in-line reservoir 22 in the inlet tube 44 provides an advantage of an improved, more continuous operation of the system, with a greater number of analysis cycles per time unit. The reservoir 22 has a preferred capacity of at least the same as the fluorometer 46 cuvette (about 3 ml in experimental model). The reservoir 22 can be merely comprised of an extended inlet tube 44, and capacity thereof is not critical to the concept of invention. The reservoir 22 shown in FIG. 1 has a capacity of about 50 ml. The During analysis of a water sample by the fluorometer 46, the reservoir 22 holds the next water sample for dark adaptation so that the system does not necessarily have to be paused. For example, each water sample can be analyzed over a 4-minute period, and the next sample can be analyzed immediately, since that sample has been in the reservoir 22 for the 4-minute period, thereby sheltered from exposure to light.

FIG. 2 shows a more complex embodiment of the invention that is particularly suitable for bodies of water 4' that are relatively turbid due to high sediment content. The electronics package 52' controls all the activities of the device. Water enters the inlet 42' and travels through the inlet tube 44' and enters a large reservoir 102, which has a preferred capacity of at least several times the capacity of the fluorometer 46 cuvette (about 3 ml in experimental model), but the capacity thereof is not critical to the concept of invention. The large reservoir 102 shown in FIG. 2 has a capacity of about 200 ml, and is configured to allow sediment to settle before sampling the water. An air purge tube 104 is connected to the top 103 of the large reservoir 102 for allowing the periodic or occasional escape of air from the system. An air purge valve 106 has an electrical connection 108 to the electronics package 52'. The air purge tube 104 has a vent opening 108 outside the buoy 10', preferably above the waterline 16, and also preferably oriented downward.

A water sampling inlet tube 110 connects to the large reservoir 102 at some point far enough from the bottom 105 thereof to be above sediment that has settled in the large reservoir 102. The water sampling tube 110 leads to the fluorometer 46 and preferably has a small, in-line reservoir 112, which has a preferred capacity of at least the same as the fluorometer cuvette (about 3 ml in experimental model), The small reservoir 112 can be merely comprised of an extended water sampling tube 110, and capacity thereof is not critical to the concept of invention. The small reservoir 112 shown in FIG. 2 has a capacity of about 50 ml.

A drain 114 for exhausting water and sediment from the large reservoir 102 and a water sampling outlet tube 116 connect through a three-way valve 116, which has an electrical connection 118 to the electronics package 52', to the outlet tube 48'. Alternatively, the drain 114 can have a discrete valve and outlet (not illustrated).

The large reservoir 102 acts as a primary stage that allows sediment to be separated from water prior to analysis by the fluorometer 46, thus reducing the amount of sediment that enters the fluorometer 46. The small reservoir 112 acts as a secondary stage that allows photosynthetic organisms within a sample of water prior to undergo a period of dark adaptation prior to analysis by the fluorometer 46. The small reservoir 112 could be omitted and the large reservoir 102 could serve both functions, with a requisite decrease in the maximum sampling rate.

The large reservoir 102 is preferably designed with turbulence promoting means such as one or more coils, baffles, or the like (not illustrated). As a fresh sample of water as it enters the reservoir 102, slight to moderate turbulence causes the fresh sample to come in contact and mix with the previous water sample which has been undergoing dark adaptation in the reservoir 102.

In one embodiment of the process, less than 10% of the newest water sample is mixed with water from the previous sample. The mixing of the two samples increases the sensitivity of the fluorescence analysis while decreasing the total time required to perform the analysis because the photosynthetic organisms from the previous sample will have completed half of a standard dark adaptation cycle. The presence of a toxic agent in the fresh sample will have a measurable effect on the physiological state of the partially dark-adapted organisms present from the previous sample. The small reservoir 112 provides means for holding static the mixed sample for completion of the dark adaptation cycle before analysis is performed.

The embodiment of the present invention shown in FIG. 2 can be operated in the following general sequence:

1. (Initial operation) With the three-way valve 116 open to the drain 114 and the pump 40 (closed to the water sampling outlet tube 116), and with the air purge valve 106 closed, the pump 40 operates for a sufficient time to draw water through the opening 42', the inlet tube 44', and into the large reservoir 102.
2. At this point, the air purge valve 106 may optionally be opened, allowing air to escape through the air purge tube 104 and out the vent opening 108, a respective volume of water entering through the inlet tube 44'. The air purge valve 106 is then closed. The pump 40 preferably does not operate during this step.

3. With the three-way valve 116 open to the water sampling outlet tube 116 and the pump 40 (closed to the drain 114), the pump 40 operates to draw water from the large reservoir 102 through the water sampling inlet tube 110, the small reservoir 112, and the fluorometer 46. This operation continues until the water in the small reservoir 112 is completely replaced. The pump is stopped to allow analysis of the sample in the fluorometer, and to allow photosynthetic organisms within the reservoir(s) 102, 112 to undergo a period of dark adaptation.

4. While and/or after the fluorometer 46 analyzes a water sample contained therein, step 1 is repeated until all of the water and sediment in the large reservoir 102 is replaced.

Figure 6:
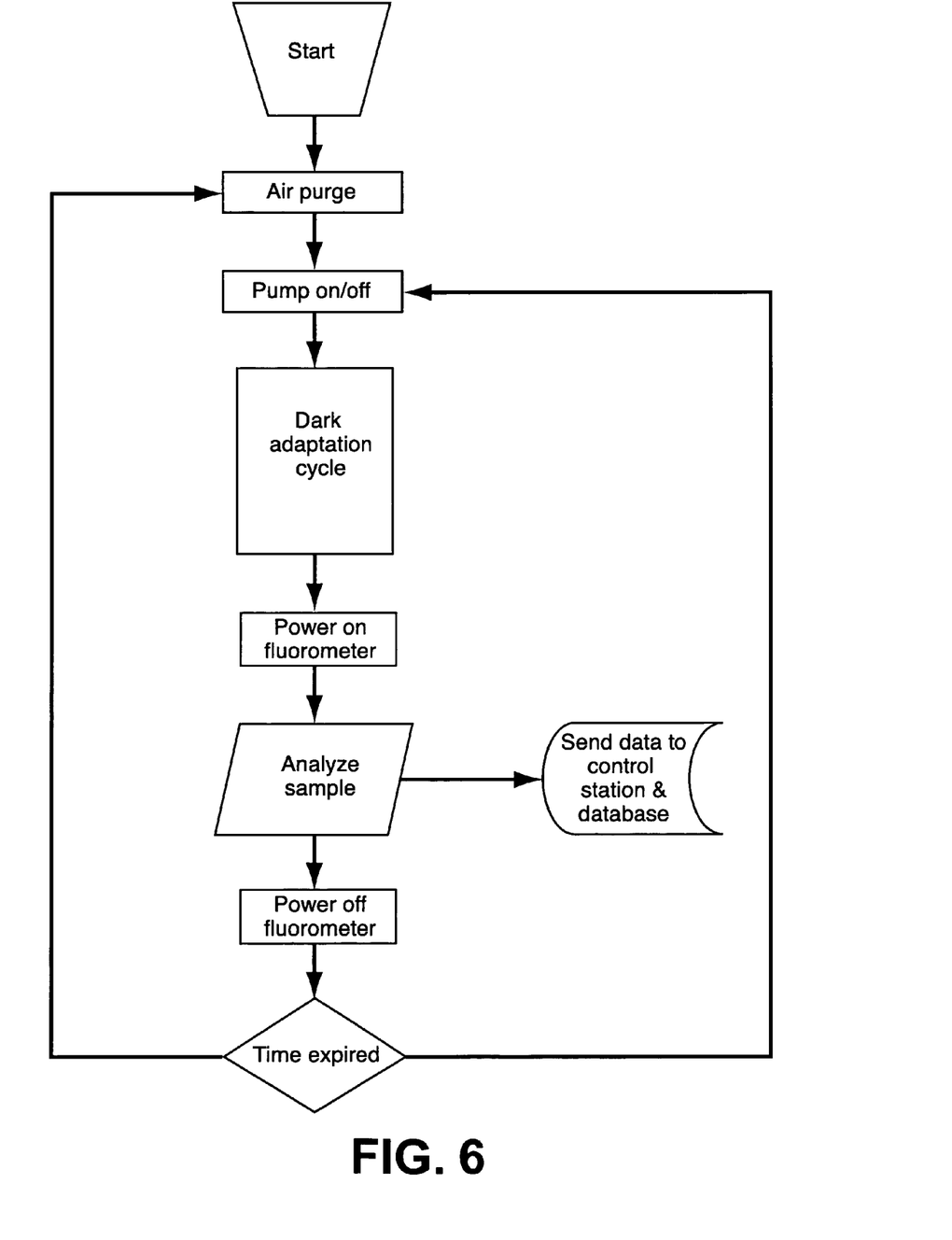
FIG. 6 is a flowchart showing a typical sampling schedule in accordance an embodiment of the present invention.

Steps 3 and 4 may be repeated many times before it is necessary to repeat step 2. All of the steps and operations are programmed into the electronics package FIG. 6 is a flowchart showing a typical sampling schedule in accordance with the present invention.

The present invention can employ a biosensor system based on fluorescence induction curves of naturally occurring freshwater algae to detect toxins such as, for example, cyanide, methyl parathion, and DCMU in primary-source water supplies under appropriate experimental conditions. In the context of current state-of-the-art biosensor research, they are unique: in the case of sunlight-exposed drinking water, the biosensors occur naturally in the medium to be protected. When combined with encrypted data telecommunication and a database-lookup library containing pertinent data for healthy algae, this approach to protection of sunlight-exposed primary drinking water supplies may be of practical value under real-world conditions.

Hydrogen cyanide is a known chemical warfare agent classified as a blood agent. The cyanide ion is an extremely toxic and fast-acting poison. Food and drinking water are the main sources of cyanide exposure for individuals not subjected to occupational exposures (Guidelines for Canadian Drinking Water Quality, 1996). Typical symptoms of cyanide poisoning are headache, nausea, weakness, palpitations, tremors, and breathlessness. In cases of severe poisoning, the nervous and respiratory systems are the first to fail. With high levels of exposure, death results from respiratory arrest. The U.S. Army has proposed field drinking water standards for cyanide of 2 and 6 mg/L, assuming a water consumption of 15 and 5/L day, respectively (Guidelines for Chemical Warfare Agents in Military Field Drinking Water, 1995). The present invention can detect cyanide concentrations well below the minimum level for human toxicity—more than six times less than the minimum lethal dose reported by Gettler and Baine (1938) and nearly 20 times less than the $LD_{50}$ value, based on consumption of 100 ml.

EXAMPLE I

Figure 3:
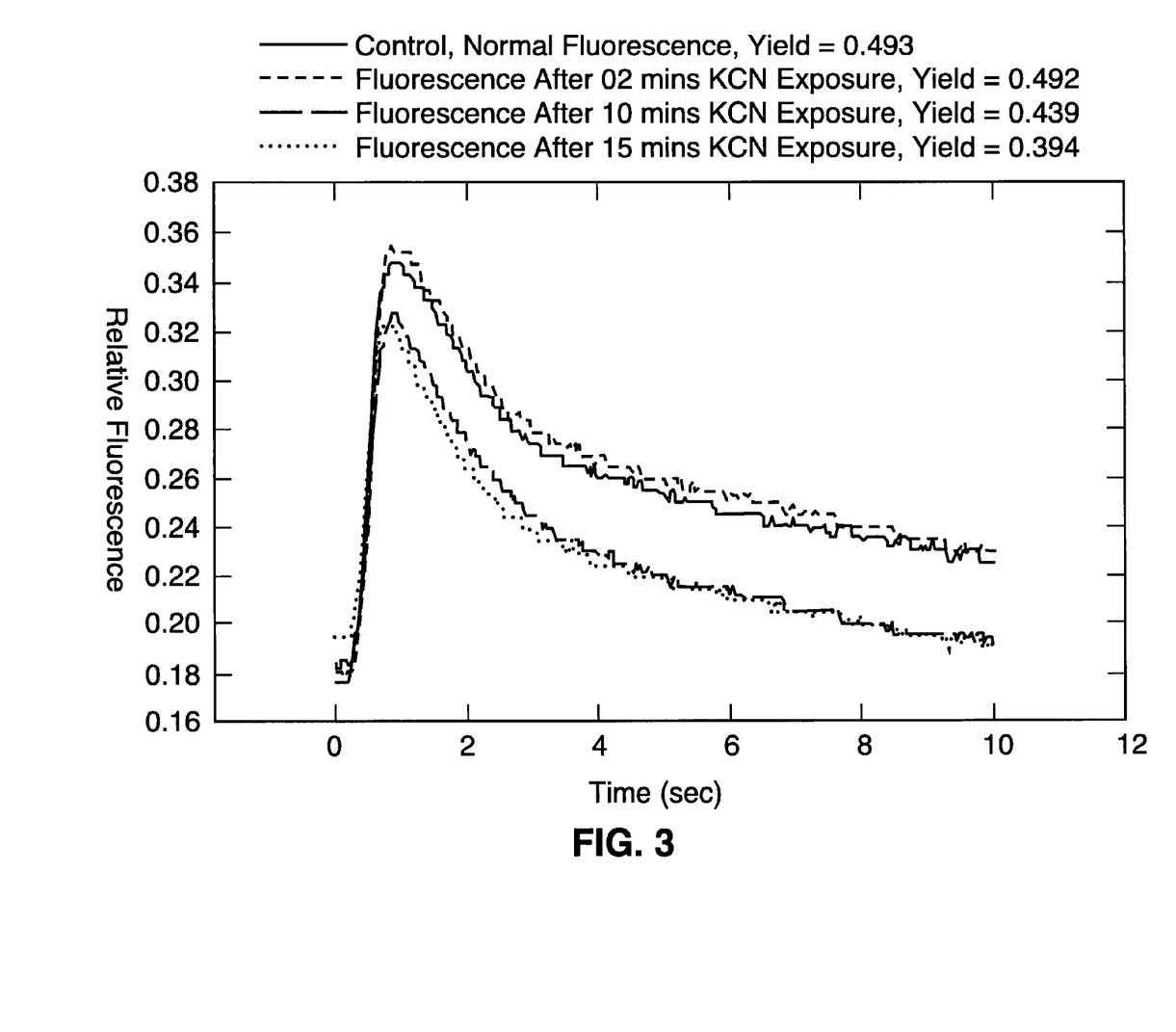
FIG. 3 is a graph showing biosensor results, including fluorescence induction curves and photochemical yield values, upon exposure of water samples from the Clinch River (Oak Ridge, Tenn.) to potassium cyanide (KCN), in accordance with the present invention.

The water-soluble salt potassium cyanide (KCN) was used to test the invention. The effect of 2 mM KCN was tested on the fluorescence emission of "as is" water samples containing naturally-occurring algae from the Clinch River. The Clinch River is the main source of drinking water for Oak Ridge, Tenn. After an initial control (no KCN) fluorescence measurement, KCN was added directly into the water sample. FIG. 3 shows the change in the fluorescence induction curve after 2, 10 and 15 min exposure of the algae to KCN compared to the control.

Methyl Parathion (MPt) is an organophosphorus insecticide used to control soil-dwelling pests and a wide range of insects and mites that infest agricultural crops. It is a cholinesterase inhibitor that is structurally and functionally similar to the chemical warfare agents classified as nerve agents (including VX and GA). Severe exposure in humans and animals can lead to convulsions, unconsciousness, cardiac arrest, and death (Guidelines for Canadian Drinking Water Quality, 1996). The present invention can detect methyl parathion concentrations well below the minimum level for human toxicity—0.005 ppm when compared to a 0.3 ppm one-day and ten-day exposure for a 10-Kg child as established by the Environmental Protection Agency (Drinking Water Standards and Health Advisories, 2002).

EXAMPLE II

Figure 4:
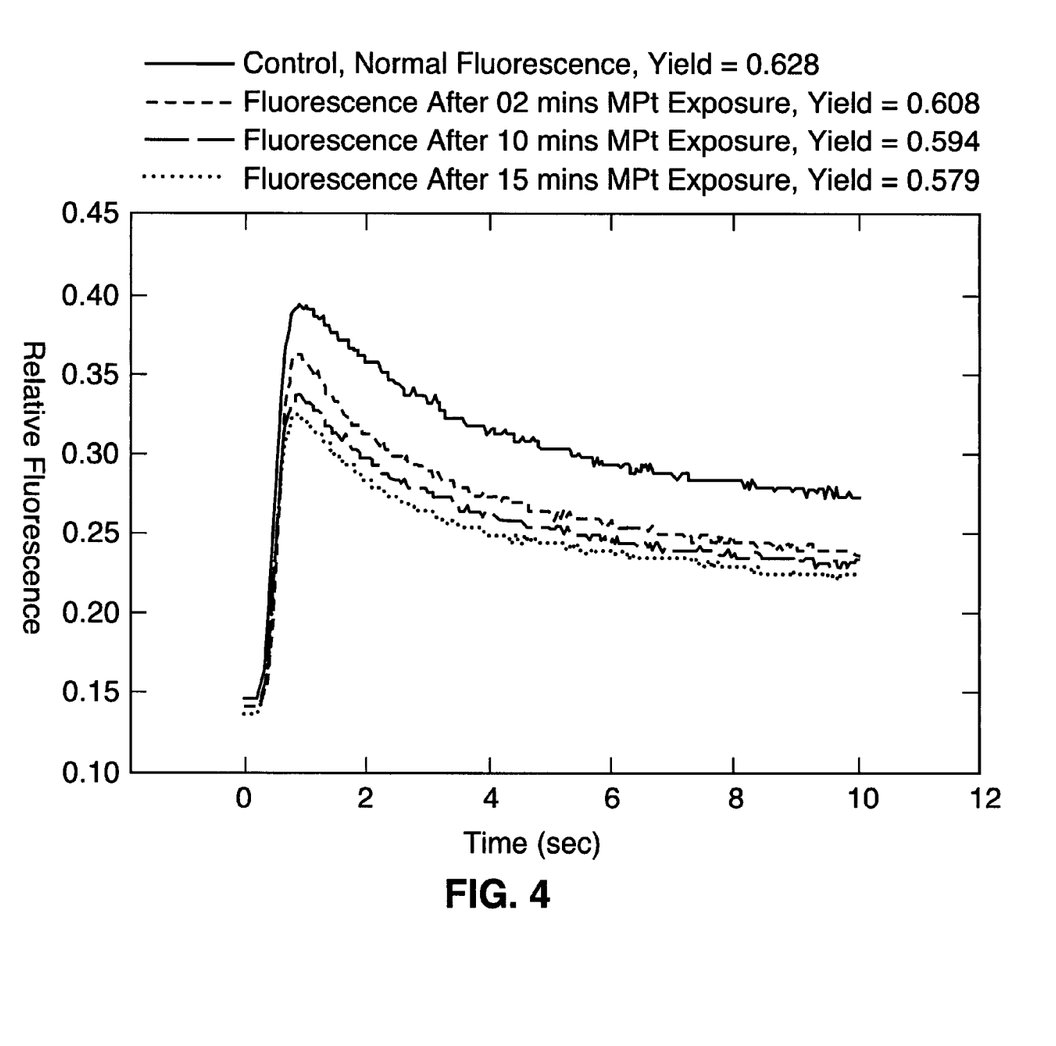
FIG. 4 is a graph showing biosensor results, including fluorescence induction curves and photochemical yield values, upon exposure of water samples from the Clinch River (Oak Ridge, Tenn.) to methyl parathion (MPt), in accordance with the present invention.

The effect of 20 μM MPt was tested on the fluorescence emission of "as is" water samples containing naturally-occurring algae from the Clinch River in Oak Ridge, Tenn. After an initial control (no MPt) fluorescence measurement, MPt was added directly into the water sample. FIG. 4 shows the change in the fluorescence induction curve after 2, 10 and 15 min exposure of the algae to MPt compared to the control.

N'-(3,4-dichlorophenyl)-N,N-dimethylurea, also known as DCMU and Diuron, is a substituted urea-based herbicide employed principally for control of vegetation in non-crop areas, including irrigation and drainage ditches. Diuron is a nonionic compound with moderate water solubility. The U.S. Environmental Protection Agency has ranked Diuron fairly high (i.e., as a Priority B Chemical) with respect to potential for groundwater contamination. Diuron is of low acute toxicity (Guidelines for Canadian Drinking Water Quality, 1996). The present invention can detect methyl parathion concentrations well below the minimum level for human toxicity—0.002 ppm when compared to a 1 ppm one-day and ten-day exposure for a 10-Kg child as established by the Environmental Protection Agency (Drinking Water Standards and Health Advisories, 2002).

EXAMPLE III

Figure 5:
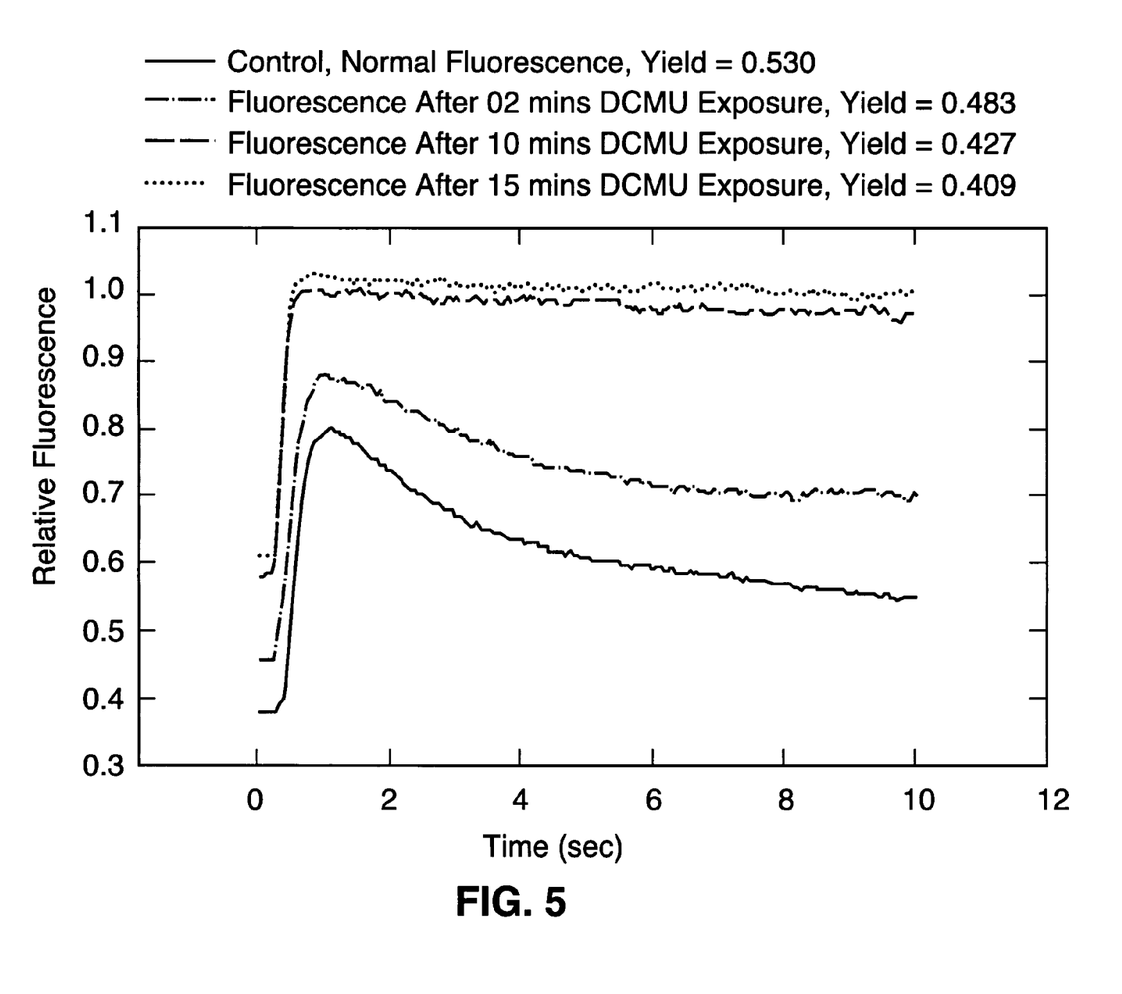
FIG. 5 is a graph showing biosensor results, including fluorescence induction curves and photochemical yield values, upon exposure of water samples from the Clinch River (Oak Ridge, Tenn.) to N'-(3,4-dichlorophenyl)-N,N-dimethylurea (DCMU), in accordance with the present invention.

The effect of 10 μM DCMU was tested on the fluorescence emission of "as is" water samples containing naturally-occurring algae from the Clinch River in Oak Ridge, Tenn. After an initial control (no DCMU) fluorescence measurement, DCMU was added directly into the water sample. FIG. 5 shows the change in the fluorescence induction curve after 2, 10 and 15 min exposure of the algae to DCMU compared to the control.

A summary of the decrease in photochemical yields measured at 0° C. with "as is" water samples containing naturally-occurring algae from the Clinch River in Oak Ridge, Tenn. is illustrated in Table 1. These results show the present invention to be effective in detecting the presence of these toxic agents in primary-source drinking water at such a low temperature.

TABLE I

Percentage (%) decrease in photochemical yield at 0° C. for naturally-occurring algae from water samples of the Clinch River, Oak Ridge, Tennessee.

| Time after exposure (mins) | 2 mM Potassium Cyanide (KCN) | 20 μM Methyl Parathion (MPt) | 10 μM DCMU |
| --- | --- | --- | --- |
| 0 | 0 | 0 | 0 |
| 2 | −0.11 | −3.19 | −8.87 |

TABLE I-continued

Percentage (%) decrease in photochemical yield at 0° C. for naturally-occurring algae from water samples of the Clinch River, Oak Ridge, Tennessee.

| Time after exposure (mins) | 2 mM Potassium Cyanide (KCN) | 20 μM Methyl Parathion (MPt) | 10 μM DCMU |
|---|---|---|---|
| 10 | −10.95 | −5.41 | −19.43 |
| 15 | −20.08 | −7.80 | −22.83 |

The present invention can include an on-board or remote computerized control program that interfaces with all electronic components of the device, records raw data from the fluorometer, and transmits a signal to a remote control station indicating the presence of general or specific toxic agents, including, but not limited to: pesticides, blood agents (e.g., cyanide), and cholinesterase inhibitors (e.g., nerve agents and similar structural compounds).

The present invention is designed to make rapid remote assessments of possible toxic contamination of source waters (reservoirs, rivers, lakes, etc.) prior to entry to drinking water distribution systems. The present invention can also be used downstream of industrial and other waste-generating facilities for regulatory purposes to make sure these facilities do not contaminate primary-source drinking water supplies. It provides around-the-clock unattended monitoring of primary-source drinking water and uses an unlimited supply of naturally occurring aquatic photosynthetic tissue as the sensing material.

The present invention can be used as a first-alert warning system for terrorist attacks on, and/or accidental spills into municipal and military drinking water supplies. The present invention can operate continuously, periodically, or responsively to an externally generated signal. An early warning alert of toxic agents is provided by the short turnaround time needed for analysis, that is, about 10 seconds to complete the fluorescence induction curve measurements. Thus, the biosensor technology can provide reports to data analysis centers in real time via wireless encrypted telecommunications, providing an early warning alert that reports the location and time of a suspected chemical attack.

The invention can be integrated into a common data highway comprising comprehensive sets of homeland security sensors to provide rapid incident management in case of a water contamination event at susceptible real-time water monitoring locations. By strategically locating and connecting water sensors on existing commercial and government infrastructures, critical information can be sent to a command center within minutes of an event.

The ultimate goal is real-time, reliable, and secure transmission and processing of data and information for the accurate prediction of the event location, identification of the threat, its directional path over time, and the number of people that could be affected. By receiving this information on a real-time basis, the command center can immediately dispatch water facility managers and first responders to the event area.

Provided with such detailed information from the common data highway, effectiveness of the first responders will be greatly enhanced. They will have fast, accurate, and precise information available relating to the type of toxic agent involved and immediately execute the appropriate treatment. Also, if necessary, areas in the projected path of the toxic agent release can be evacuated in advance. The enhanced water monitoring system can be integrated to assure an ultra-high level of reliability, survivability and security, especially where the common data highway is scalable across state, local, and federal governments.

See, for example, commonly assigned U.S. patent application Ser. No. 10/370,913 filed on Feb. 21, 2003 entitled "System for Detection of Hazardous Events", the entire disclosure of which is incorporated herein by reference.

While there has been shown and described what are at present considered the preferred embodiments of the invention, it will be obvious to those skilled in the art that various changes and modifications can be prepared therein without departing from the scope of the inventions defined by the appended claims.

What is claimed is:

1. A device for detecting toxic agents in a liquid medium comprising:
a body comprising at least one portion that is submerged into a liquid medium, an inlet for introducing a sample of the liquid medium to an interior of the body, and an outlet for ejecting the sample of the liquid medium;
a first reservoir within said body comprising a first opening in an upper surface of the first reservoir, a second opening present in a sidewall of the first reservoir, and a first reservoir drain present in a base surface of the first reservoir, wherein the inlet in the body is in fluid communication with the first opening of the first reservoir;
a fluorometer for measuring photosynthetic activity of organisms in the sample of the liquid medium, the fluorometer comprising an inlet in fluid communication with the second opening of the first reservoir and a fluorometer drain;
a pump in fluid communication with the fluorometer drain, the first reservoir drain, and the outlet of the body;
a valve system configured to open and close the fluorometer drain and the first reservoir drain; and
an electronics package in communication with the valve system, the pump and the fluorometer, wherein during a first time period the electronics package is configured to activate the pump, close the fluorometer and open the reservoir drain to draw the sample of liquid medium into the reservoir, and during a second time period the electronics package is configured to open the drain from the fluorometer and close the reservoir drain to draw the sample of the liquid medium into the fluorometer for the measuring of the photosynthetic activity of photosynthetic organisms in the sampe of the liquid medium, and during a third time period the electronics package is configured to close the drain from the fluorometer and open the drain from the sample reservoir to expel the sample of the liquid medium through the outlet of the body so that less than 10% of a subsequent sample is mixed with the sample of the liquid medium.

2. The device of claim 1, wherein the body comprises a bouy.

3. The device of claim 1 comprising a fuel cell or a battery.

4. The device of claim 1 comprising a solar panel present on an exterior of the body.

5. The device of claim 1, wherein the first reservoir comprises a turbulence promoting apparatus.

6. The device of claim 5, wherein the turbulence promoting apparatus comprises baffles, coils or a combination thereof.

7. The device of claim 1, wherein the first reservoir comprises an air purge tube extending from the upper surface of the first reservoir to an exterior of the body.

8. The device of claim 1, wherein the fluid communication between the first reservoir and the fluorometer is a provided by a sample tube comprising a second reservoir, the second reservoir having a volume less than the first reservoir.

9. The device of claim 8, wherein the second reservoir has a volume substantially equal to a cuvette of the fluorometer.

10. The device of claim 8, wherein the second reservoir holds the sample of the liquid medium for completion of a dark adaptation cycle of the organisms prior to the measuring photosynthetic activity of the organisms by the fluorometer.

11. The device of claim 8, wherein the second opening present in the sidewall of the first reservoir is present at a height to prohibit sedimentation to enter the fluorometer.

12. The device of claim 8 comprising an antennae for transmitting data produced by the transmitter.

13. The device of claim 8, wherein the fluorometer detects a presence of cyanide, methyl parathion, N'-(3,4-dichlorophenyl)-N,N-dimethylurea or a combination thereof.

14. The device of claim 1, wherein the valve system comprises a thee-way valve.

15. The device of claim 1, wherein the electronics package stops the pump during the measuring photosynthetic activity of organisms in the sample of the liquid medium.

* * * * *

UNITED STATES PATENT AND TRADEMARK OFFICE
CERTIFICATE OF CORRECTION

PATENT NO. : 7,591,979 B2 Page 1 of 1
APPLICATION NO. : 10/689316
DATED : September 22, 2009
INVENTOR(S) : David E. Hill et al.

It is certified that error appears in the above-identified patent and that said Letters Patent is hereby corrected as shown below:

Title Page, Item (75) Inventors should read

-- Inventors: David E. Hill, Knoxville, TN (US); Miguel Rodriguez, Jr., Oak Ridge, TN (US); Elias Greenbaum, Knoxville, TN (US) --.

Signed and Sealed this

Sixteenth Day of February, 2010

David J. Kappos
*Director of the United States Patent and Trademark Office*